(12) United States Patent
Osada et al.

(10) Patent No.: US 9,826,890 B2
(45) Date of Patent: Nov. 28, 2017

(54) ENDOSCOPE AND MANUFACTURING METHOD OF ENDOSCOPE

(71) Applicant: Panasonic Intellectual Property Management Co., Ltd., Osaka (JP)

(72) Inventors: Akinori Osada, Fukuoka (JP);
Takafumi Sanada, Fukuoka (JP);
Yasuyuki Hanada, Fukuoka (JP);
Naoyuki Haraguchi, Saga (JP);
Takahisa Suzuki, Fukuoka (JP); Tooru Tanaka, Fukuoka (JP); Hiroshi Nagayasu, Fukuoka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 203 days.

(21) Appl. No.: 14/625,394

(22) Filed: Feb. 18, 2015

(65) Prior Publication Data

US 2015/0238069 A1   Aug. 27, 2015

(30) Foreign Application Priority Data

Feb. 27, 2014   (JP) ................................. 2014-037385
May 30, 2014   (JP) ................................. 2014-113260

(51) Int. Cl.
  *A61B 1/05*  (2006.01)
  *A61B 1/00*  (2006.01)
  (Continued)

(52) U.S. Cl.
  CPC .............. *A61B 1/05* (2013.01); *A61B 1/0011* (2013.01); *A61B 1/00096* (2013.01);
  (Continued)

(58) Field of Classification Search
  CPC ..... A61B 1/05; A61B 1/00096; A61B 1/0011; A61B 1/00163; A61B 1/055; A61B 1/051; G02B 23/2423; G02B 23/2476
  See application file for complete search history.

(56) References Cited

U.S. PATENT DOCUMENTS 4,984,878 A    1/1991  Miyano
5,554,099 A *  9/1996  Heimberger ....... G02B 23/2446
                                              600/160
(Continued)

FOREIGN PATENT DOCUMENTS

CN    103492927 A    1/2014
EP    2 148 232 A1   1/2010
(Continued)

OTHER PUBLICATIONS

Extended European Search Report dated Jul. 3, 2015, for corresponding EP Application No. 15156598.3-1660, 10 pages.
(Continued)

*Primary Examiner* — Timothy J Neal
(74) *Attorney, Agent, or Firm* — Seed IP Law Group LLP

(57) ABSTRACT

An endoscope which promotes downsizing and cost reduction, and a manufacturing method of an endoscope are provided. For this reason, in an endoscope, a lens unit containing a lens in a lens tube, an image capturing element of which an image capturing surface is covered with element cover glass, and an adhesive resin fixing the lens unit of which an optical axis of the lens is coincident with the center of the image capturing surface to the element cover glass with a separation portion are disposed.

11 Claims, 15 Drawing Sheets

(51) Int. Cl.
  *G02B 23/24* (2006.01)
  *G02B 7/02* (2006.01)
(52) U.S. Cl.
  CPC ......... *G02B 7/025* (2013.01); *G02B 23/2423* (2013.01); *G02B 23/2476* (2013.01)

(56) References Cited

U.S. PATENT DOCUMENTS

| | | | |
|---|---|---|---|
| 5,781,350 | A | 7/1998 | Tachihara et al. |
| 7,379,252 | B2 | 5/2008 | Murayama |
| 8,243,129 | B2 | 8/2012 | Uzawa |
| 8,582,217 | B2 | 11/2013 | Katakura |
| 2006/0221457 | A1 | 10/2006 | Murayama |
| 2007/0167841 | A1* | 7/2007 | Hayashi ............... C03C 27/10 600/476 |
| 2010/0022841 | A1 | 1/2010 | Takahashi et al. |
| 2010/0085466 | A1 | 4/2010 | Fujimori et al. |
| 2010/0165134 | A1 | 7/2010 | Dowski, Jr. et al. |
| 2012/0007972 | A1 | 1/2012 | Uzawa |
| 2013/0215523 | A1 | 8/2013 | Katakura |
| 2013/0329026 | A1 | 12/2013 | Hida et al. |
| 2015/0065798 | A1* | 3/2015 | Kuroda ............... A61B 1/00096 600/109 |
| 2015/0238069 | A1 | 8/2015 | Osada et al. |

FOREIGN PATENT DOCUMENTS

| | | |
|---|---|---|
| EP | 2 680 059 A1 | 1/2014 |
| JP | 02-176611 A | 7/1990 |
| JP | 03-012124 A | 1/1991 |
| JP | 09-262207 A | 10/1997 |
| JP | 2001-128930 A | 5/2001 |
| JP | 3426378 B2 | 7/2003 |
| JP | 2006-276779 A | 10/2006 |
| JP | 2010-022617 A | 2/2010 |
| JP | 2010-091986 A | 4/2010 |
| JP | 2010-164718 A | 7/2010 |
| JP | 2012-139308 A | 7/2012 |
| JP | 5270054 B1 | 8/2013 |
| JP | 2013-200537 A | 10/2013 |
| JP | 2014-036799 A | 2/2014 |
| JP | 2014-191222 A | 10/2014 |
| JP | 2015-177984 A | 10/2015 |
| WO | 2011/070897 A1 | 6/2011 |
| WO | 2013/031276 A1 | 3/2013 |
| WO | 2013/146091 A1 | 10/2013 |

OTHER PUBLICATIONS

Materne et al.,"Organosilane Technology in Coating Applications: Review and Perspectives" Dow Corning, 2012, retrieved on Mar. 19, 2015, from http://www.dowcorning.com/content/publishedlit/26-1402-01.pdf, 16 pages.

Chinese Search Report, dated Jun. 2, 2017, for corresponding Chinese Application No. 201510089971.2, 2 pages.

* cited by examiner

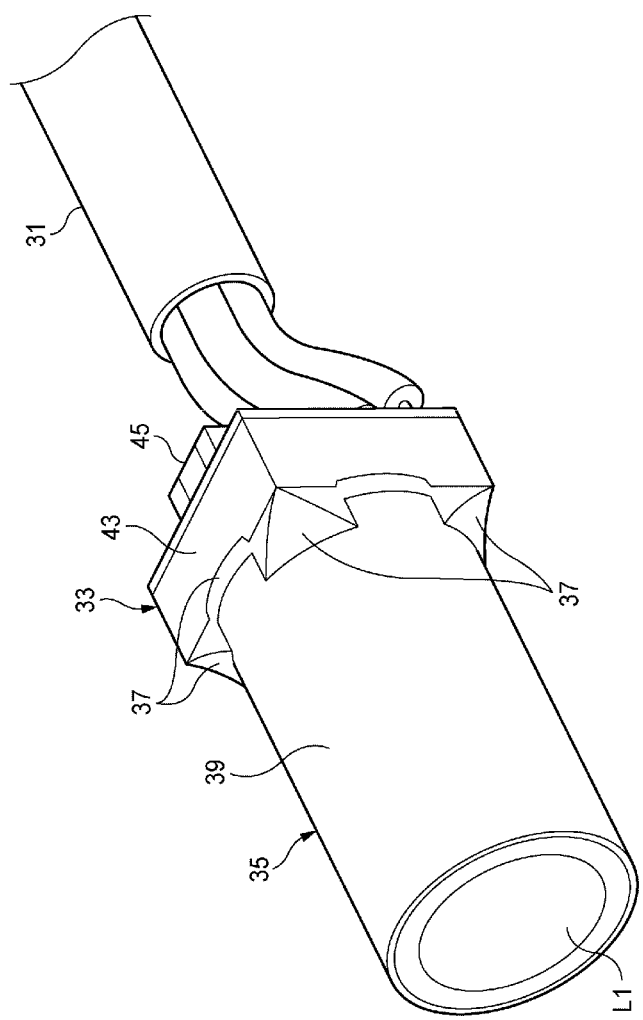

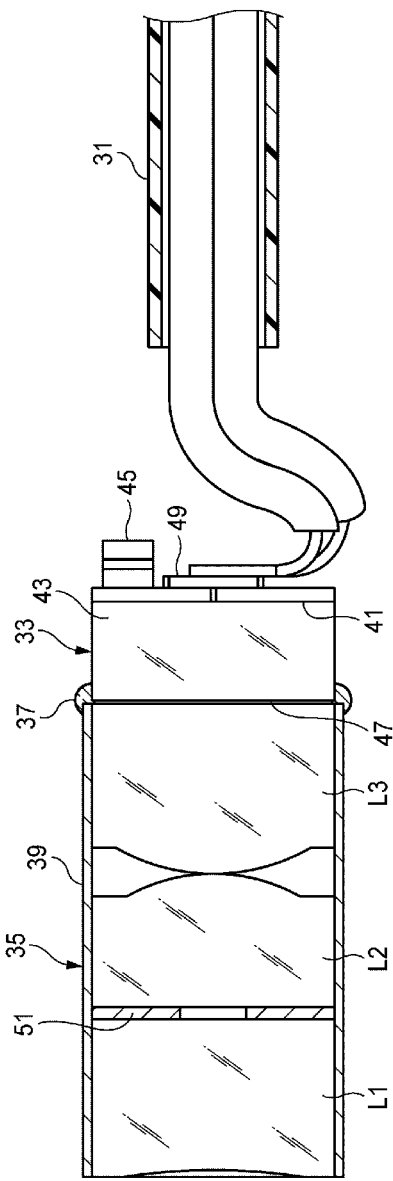

ENDOSCOPE AND MANUFACTURING METHOD OF ENDOSCOPE

BACKGROUND OF THE INVENTION

1. Field of the Invention

The present invention relates to an endoscope and a manufacturing method of an endoscope, and in particular, relates to a small diameter endoscope which promotes downsizing and cost reduction, and for example, is used for surgery, and a manufacturing method of an endoscope.

2. Description of the Related Art

In the related art, an endoscope for capturing an image of an internal body of a patient, and an inner portion of an instrument or a structure has become widespread in a medical field or an industrial field. In an insertion portion of such an endoscope which is inserted into an inner portion of an observation target, light from an image capturing portion forms an image on a light receiving surface of an image sensor by an objective lens system, and the image forming light is converted into an electric signal and transmitted to an external image processing device or the like through a signal cable as a projected image signal. In a hard portion disposed in a leading end of such an endoscope, a plurality of components such as an image capturing element, and an optical element, for example, a lens forming a light image on an image capturing surface of the image capturing element is arranged. Recently, in an endoscope having such a complicated configuration, it is important to more easily manufacture the endoscope and to further decrease an outer diameter for reducing a burden of a person to be treated.

For example, in Japanese Patent. Unexamined Publication No. 3-12124, an electronic endoscope forms a concave portion in a substrate, and includes a solid image capturing element in the concave portion. A conductive line is installed between the solid image capturing element and an upper surface side of a step portion in the substrate. The conductive line portion is sealed with a resin, and a glass plate is adhered to the light receiving surface of the solid image capturing element. A frame is disposed on the substrate by being secured in contact with an outside portion from a connection portion of the conductive line. Then, the frame is secured to a barrel of an objective lens.

In the electronic endoscope having the configuration described above, the glass plate is bonded to the light receiving surface of the solid image capturing element, the frame is secured in contact with the substrate, and the barrel of the objective lens is secured to the frame. Accordingly, a reduction in a diameter of the insertion portion and a reduction in a length of a leading end hard portion in an axis direction are promoted.

In the above-described electronic endoscope of an example of the related art, the frame is secured to the substrate, and the frame is secured to the barrel of the objective lens, and thus a diameter greater than or equal to that of the solid image capturing element is required, and it is difficult to reduce the diameter. In addition, the number of components increases, and thus the cost also increases.

SUMMARY OF THE INVENTION

An object of the present invention is to provide an endoscope which promotes downsizing and cost reduction, and a manufacturing method of an endoscope.

According to an aspect of the present invention, there is provided an endoscope including a lens unit containing a lens in a lens tube; an image capturing element including an image capturing surface which is covered with element cover glass; and an adhesive resin fixing the lens unit in which an optical axis of the lens is coincident with the center of the image capturing surface to the element cover glass with a separation portion.

According to another aspect of the present invention, there is provided a manufacturing method of an endoscope including applying a UV thermosetting resin to at least one of a lens unit and an image capturing element; supporting the lens unit; positioning an optical axis of the lens unit and the center of an image capturing surface of the image capturing element by referring to an image captured by the image capturing element while moving the image capturing element supported on an XYZ stage, and positioning a direction along the optical axis of the lens unit and the image capturing element; temporarily fixing the lens unit to the image capturing element with the UV thermosetting resin by ultraviolet irradiation; and then permanently fixing the lens unit to the image capturing element with the UV thermosetting resin by heat treatment.

According to the aspects of the present invention, it is possible to promote downsizing and cost reduction in an endoscope.

BRIEF DESCRIPTION OF DRAWINGS

FIG. 5 is a perspective view illustrating a configuration of a leading end portion of an endoscope according to a second exemplary embodiment;

FIG. 7A is a cross-sectional view of a leading end portion of an endoscope according to a fifth exemplary embodiment;

DETAILED DESCRIPTION OF THE PREFERRED EMBODIMENTS

Hereinafter, exemplary embodiments (hereinafter, referred to as "this exemplary embodiment") of an endoscope and a manufacturing method of an endoscope according to the present invention will be described in detail with reference to the drawings.

Figure 1:
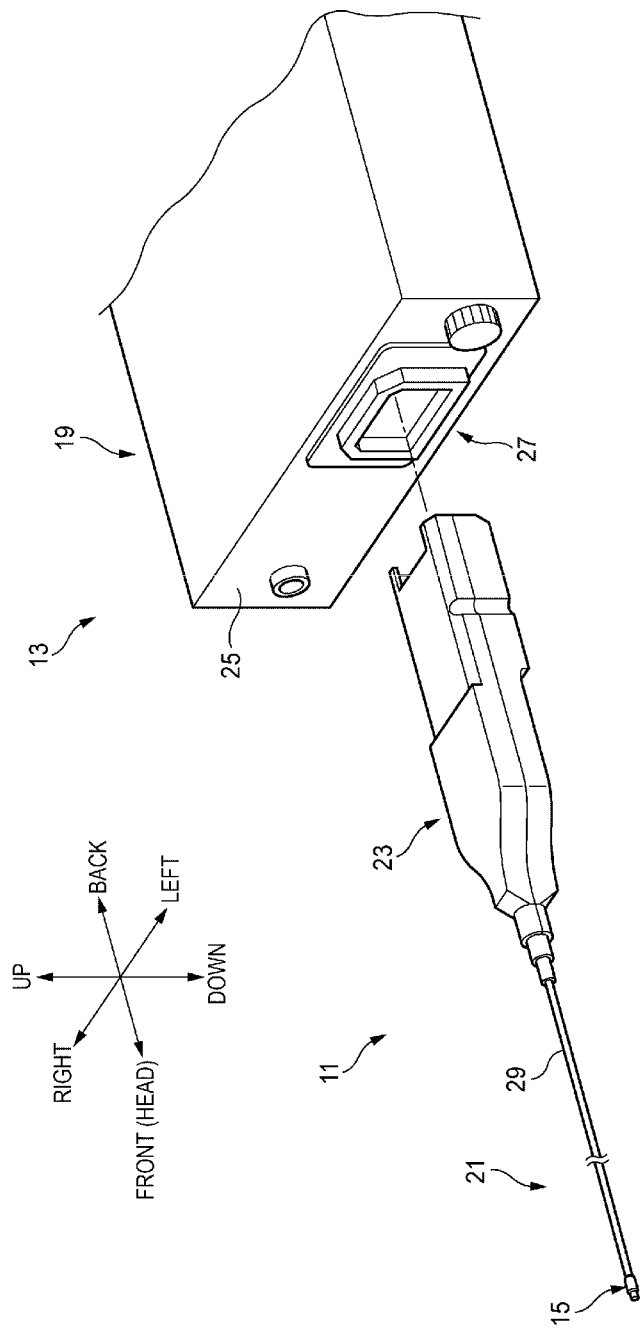
FIG. 1 is an entire configuration diagram of an endoscope system using an endoscope according to an exemplary embodiment of the present invention.
Figure 2:
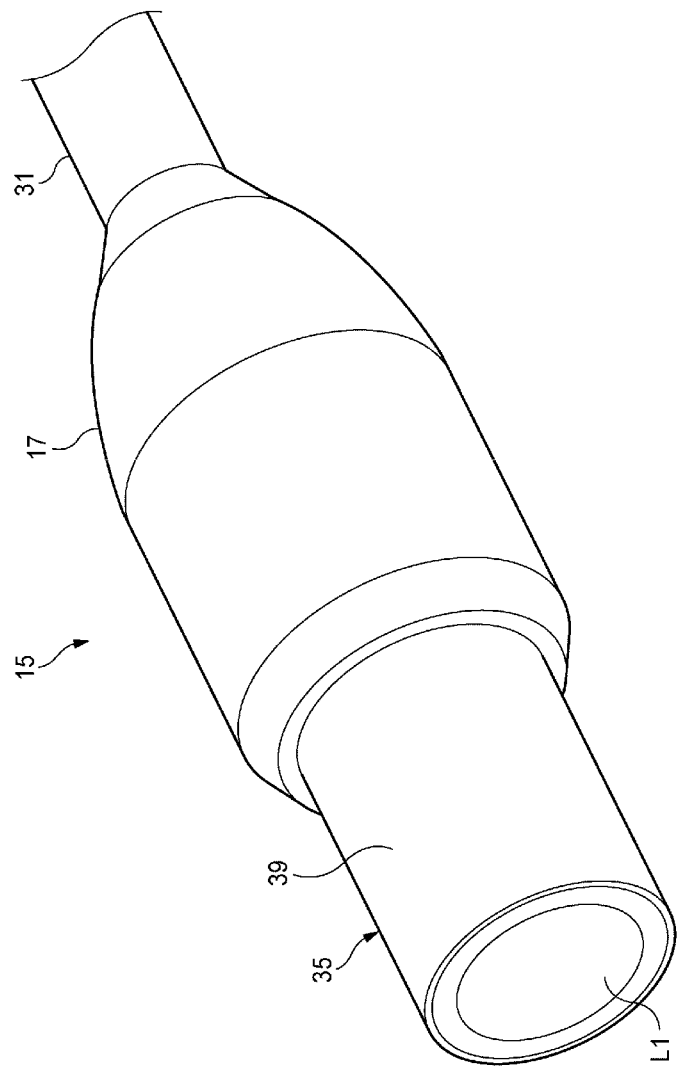
FIG. 2 is a perspective view illustrating a configuration of a leading end portion of the endoscope of this exemplary embodiment.
Figure 3:
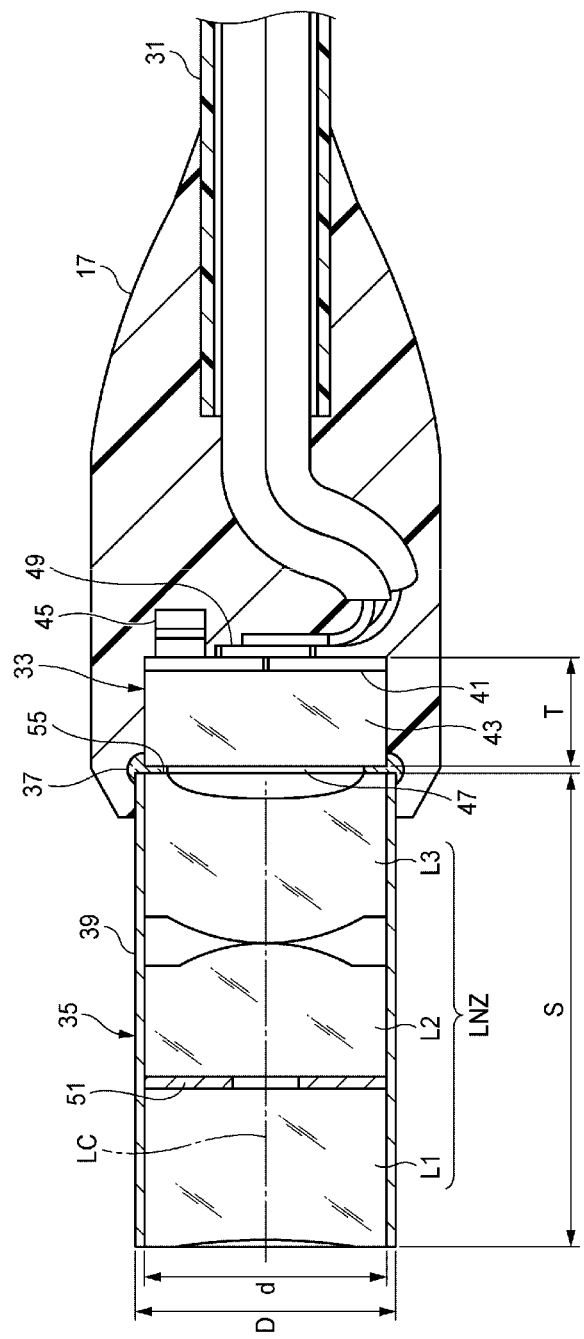
FIG. 3 is a cross-sectional view of a leading end portion of an endoscope according to a first exemplary embodiment.
Figure 4:
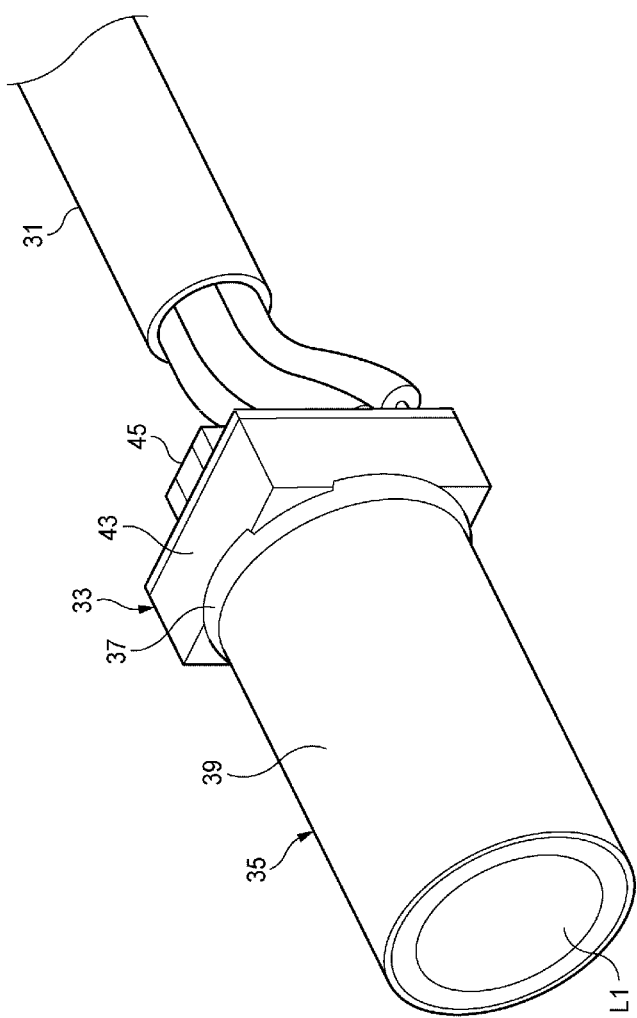
FIG. 4 is a perspective view illustrating a configuration of a portion excluding a mold resin from the leading end portion of the endoscope according to the first exemplary embodiment.

FIG. 1 is an entire configuration diagram of an endoscope system using an endoscope according to an exemplary embodiment of the present invention. FIG. 2 is a perspective view illustrating a configuration of a leading end portion of the endoscope of this exemplary embodiment. FIG. 3 is a cross-sectional view of a leading end portion of an endoscope according to a first exemplary embodiment. FIG. 4 is a perspective view illustrating a configuration of a portion excluding a mold resin from the leading end portion of the endoscope according to the first exemplary embodiment.

In FIG. 1, an entire configuration of endoscope system 13 including endoscope 11 and video processor 19 is illustrated as a perspective view. In FIG. 2, a configuration of leading end portion 15 of endoscope 11 illustrated in FIG. 1 is illustrated as a perspective view. In FIG. 3, a configuration of leading end portion 15 illustrated in FIG. 2 is illustrated as a cross-sectional view. In FIG. 4, a configuration excluding mold resin 17 from leading end portion 15 illustrated in FIG. 2 is illustrated as a perspective view.

Furthermore, a direction herein which is used for description accords to a direction illustrated in each drawing. Here, "Up" and "Down" respectively correspond to an upper portion and a lower portion of video processor 19 placed on a horizontal plane, and "front (head)" and "back" respectively correspond to a leading end side of insertion portion 21 and a base end side of plug portion 23 in an endoscope main body (hereinafter, referred to as "endoscope 11").

As illustrated in FIG. 1, endoscope system 13 includes endoscope 11 which is a flexible scope used for medical purposes, and video processor 19 which performs known image processing or the like with respect to a still image and a moving image obtained by capturing an image of an inner portion of an observation target (here, a human body). Endoscope 11 extends in an approximately front and back direction, and includes insertion portion 21 which is inserted into the inner portion of the observation target, and plug portion 23 to which a back portion of insertion portion 21 is connected.

Video processor 19 includes socket portion 27 which is opened in front wall 25 of video processor 19. The back portion of plug portion 23 of endoscope 11 is inserted into socket portion 27, and thus endoscope 11 is able to transmit and receive electric power and various signals (a projected image signal, a control signal, and the like) to and from video processor 19.

The above-described electric power and the various signals are led to soft portion 29 from plug portion 23 through transmission cable 31 (refer to FIG. 3) inserted into an inner portion of soft portion 29. Image data output by image capturing element 33 disposed in leading end portion 15 is transmitted to video processor 19 from plug portion 23 through transmission cable 31. Then, video processor 19 performs image processing such as color correction, and tone correction with respect to the received image data, and outputs the image processed image data to a display device (not illustrated). The display device, for example, is a monitor device including a display device such as a liquid crystal display panel, and displays an image of a photographic subject captured by endoscope 11.

As illustrated in FIG. 3, endoscope 11 according to this exemplary embodiment includes lens unit 35, image capturing element 33, and adhesive resin 37 in leading end portion 15. Lens unit 35 contains a lens in lens tube 39. Image capturing surface 41 of image capturing element 33 is covered with element cover glass 43. Capacitor for electrostatic countermeasure 45 is attached to a surface of image capturing element 33 opposite to element cover glass 43. Adhesive resin 37, for example, is configured of a UV thermosetting resin. Adhesive resin 37 fixes lens unit 35 in which an optical axis of the lens is coincident with the center of image capturing surface 41 to element cover glass 43 with separation portion 47. Accordingly, lens unit 35 is directly adhered and fixed to image capturing element 33 by adhesive resin 37. In order to obtain final hardness, for example, it is necessary that adhesive resin 37 is subjected to a heat treatment, and adhesive resin 37 is an adhesive agent which is cured until hardness due to ultraviolet irradiation is obtained.

Insertion portion 21 includes flexible soft portion 29 of which a back end is connected to plug portion 23, and leading end portion 15 which is continued to a leading end of soft portion 29. Soft portion 29 has a suitable length corresponding to need such as various endoscopic inspections and endoscope surgeries. The largest outer diameter of leading end portion 15, for example, is approximately 1.5 mm.

As illustrated in FIG. 3, leading end portion 15 includes image capturing element 33, and tubular lens tube 39 including the lens or the like, and includes lens unit 35 supporting image capturing element 33 on a back end, and circuit substrate 49 mounted on a back portion of image capturing element 33. Lens tube 39, for example, is formed of metal, and leading end portion 15 includes the hard portion by using a hard material in lens tube 39.

Transmission cable 31 is electrically connected to a back portion of circuit substrate 49, and a connection portion of circuit substrate 49 is covered with mold resin 17 for sealing. Furthermore, in the following description, a term of "adhesive agent" does not strictly indicate a substance used for adhering a surface to a surface of a solid substance, but widely indicates a substance which is able to be used for coupling two substances, or a substance having a function as a sealing material when a cured adhesive agent has high barrier properties with respect to gas and liquid.

In lens tube 39, a plurality of (in an illustrated example, three) lenses L1 to L3 which are formed of an optical material (glass, a resin, or the like), and diaphragm member 51 which is interposed between lens L1 and lens L2 are embedded in a state where the plurality of lenses L1 to L3 and diaphragm member 51 are closely in contact with each other in a direction of optical axis LC. Lens L1 and lens L3 are fixed to an inner circumferential surface of lens tube 39 over the entire circumference by an adhesive agent. A front end of lens tube 39 is hermetically closed (sealed) by lens L1, and a back end is hermetically closed by lens L3, and thus an inner portion of lens tube 39 is not invaded by air, moisture, or the like. Accordingly, air or the like is not able to be pulled from one end of lens tube 39 to the other end. Furthermore, in the following description, lenses L1 to L3 are collectively referred to as optical lens group LNZ.

As a metal material configuring lens tube 39, for example, nickel is used. Nickel has a comparatively high rigidity modulus and high corrosion resistance, and is suitable as a material configuring leading end portion 15. Instead of nickel, for example, a copper nickel alloy may be used. A copper nickel alloy also has high corrosion resistance, and is suitable as a material configuring leading end portion 15. In addition, as the metal material configuring lens tube 39, a material which is able to be manufactured by electrocasting (electroplating) is preferably selected. Here, the reason for using electrocasting is because dimensional accuracy of a member manufactured by the electrocasting is extremely high at less than 1 μm (so-called sub-micron accuracy), and variation is also reduced at the time of manufacturing a plurality of members. As described later, lens tube 39 is an extremely small member, and an error in inner and outer diameter dimensions affects optical performance (image quality) of endoscope 11. Lens tube 39, for example, is configured of an electrocasted nickel tube, and thus even if the diameter is reduced, endoscope 11 is obtained in which high dimensional accuracy is able to be ensured, and an image having high image quality is able to be captured.

As illustrated in FIG. 3 and FIG. 4, image capturing element 33, for example, is configured of an image capturing device such as a small Charge Coupled Device (CCD) or a small Complementary Metal-Oxide Semiconductor (CMOS) which is in the shape of a square when seen from the front and back directions. Light incident from the outside forms an image on image capturing surface 41 of image capturing element 33 by optical lens group LNZ in the lens tube. Circuit substrate 49 mounted in the back portion (a rear surface side) of image capturing element 33 has an outer shape which is slightly smaller than image capturing element 33 when seen from a back side. Image capturing element 33, for example, includes a Land Grid Array (LGA) in a rear surface, and is electrically connected to an electrode pattern formed on circuit substrate 49.

In addition, as illustrated in FIG. 2, in endoscope 11, the entire image capturing element 33 and at least a part of lens unit 35 on image capturing element 33 side are covered with mold resin 17.

Next, a modification example in which a part of the configuration of endoscope 11 is changed will be described as another exemplary embodiment.

FIG. 5 is a perspective view illustrating a configuration of a leading end portion of an endoscope according to a second exemplary embodiment. In the second exemplary embodiment, a first modification example of the configuration of leading end portion 15 of the endoscope illustrated in FIG. 3 and FIG. 4 is illustrated.

In order to improve the strength of four corners of image capturing element 33, as illustrated in FIG. 5, adhesive resin 37 is additionally disposed in the endoscope of the second exemplary embodiment. In this case, image capturing element 33 is positioned in a back end of lens unit 35, and then adhesive resin 37 is applied to four portions (in FIG. 5, three portions among the four portions are illustrated) facing corner portions of image capturing element 33 in a back end portion of lens unit 35 which are in contact with image capturing element 33. In this state, an applied portion of adhesive resin 37 is exposed, and adhesive resin 37 is cured by ultraviolet irradiation for a short period of time such as a few seconds, and thus it is possible to reduce the time required for a process. According to the configuration of the first modification example, strength of an adhesion portion between image capturing element 33 and lens unit 35 increases.

Figure 6A:
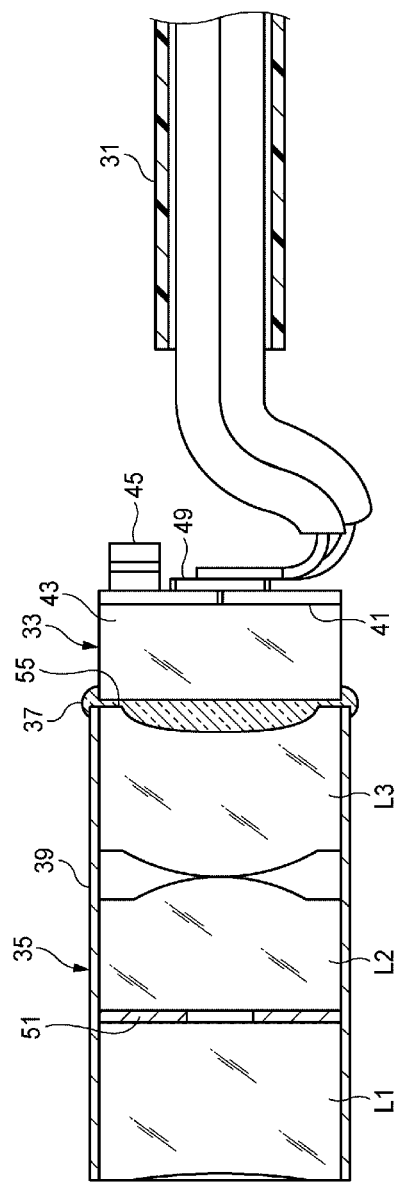
FIG. 6A is a cross-sectional view of a configuration according to a third exemplary embodiment in which a separation portion is filled with an adhesive resin.
Figure 6B:
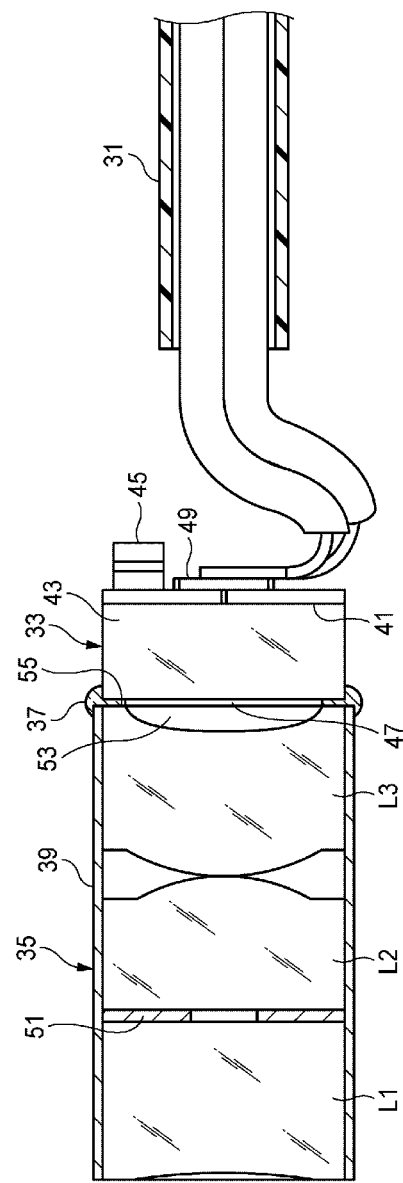
FIG. 6B is a cross-sectional view of a configuration according to a fourth exemplary embodiment in which an air layer is disposed in a separation portion.

FIGS. 6A and 6B are diagrams illustrating a third exemplary embodiment and a fourth exemplary embodiment as another modification example of the leading end portion of the endoscope, FIG. 6A is a cross-sectional view of a configuration according to a third exemplary embodiment in which a separation portion is filled with an adhesive resin, and FIG. 6B is a cross-sectional view of a configuration according to a fourth exemplary embodiment in which an air layer is disposed in a separation portion. The third exemplary embodiment illustrates a second modification example of the configuration of the leading end portion of the endoscope, and the fourth exemplary embodiment illustrates a third modification example of the configuration of the leading end portion of the endoscope.

In the endoscope of the third exemplary embodiment (the second modification example), as illustrated in FIG. 6A, separation portion 47 between lens unit 35 and element cover glass 43 is filled with adhesive resin 37. As in an illustrated example, when a final surface of lens L3 on an image capturing side includes a concave surface in a surface facing element cover glass 43, a space between a flat surface of element cover glass 43 and the concave surface of lens L3, for example, is filled with adhesive resin 37 having light transmissivity such as transparence. In this case, a distance between edge portion 55 of a lens circumferential edge of second surface L3R2 of lens L3 and element cover glass 43, for example, is 0 to 100 μm. In the configuration of the second modification example, it is possible to further improve the strength of the adhesion portion by being filled with adhesive resin 37. Furthermore, a final surface of lens L3 on the image capturing side which is a surface facing element cover glass 43 may include a convex surface. When the convex surface is included, the distance between a center portion of second surface L3R2 of lens L3 and element cover glass 43, for example, is 0 to 100 μm.

In the endoscope of the fourth exemplary embodiment (the third modification example), as illustrated in FIG. 6B, air layer 53 is disposed in separation portion 47 between lens unit 35 and element cover glass 43. As in an illustrated example, when the final surface of lens L3 on the image capturing side includes the concave surface in the surface facing element cover glass 43, air layer 53 is formed between a flat surface of element cover glass 43 and the concave surface of lens L3 without being filled with adhesive resin 37. In this case, the distance between edge portion 55 of the lens circumferential edge of second surface L3R2 of lens L3 and element cover glass 43, for example, is 0 to 100 μm. In the configuration of the fourth exemplary embodiment, a refractive index difference in the final surface of lens unit 35 on the image capturing side increases by disposing air layer 53, and freedom for designing the lens increases.

Figure 7B:
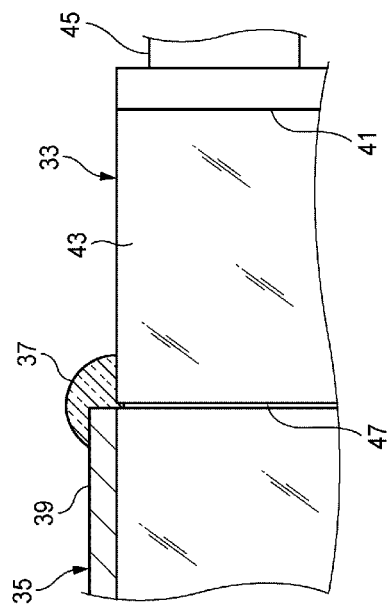
FIG. 7B is an enlarged view of a main part of the leading end portion of the endoscope according to the fifth exemplary embodiment.

FIGS. 7A and 7B are diagrams illustrating a configuration of a leading end portion of an endoscope according to a fifth exemplary embodiment, FIG. 7A is a cross-sectional view of the leading end portion, and FIG. 7B is an enlarged view of a main part of FIG. 7A. The fifth exemplary embodiment illustrates a fourth modification example of the configuration of the leading end portion of the endoscope.

In the endoscope of the fifth exemplary embodiment (the fourth modification example), the final surface of lens L3 of lens unit 35 on the image capturing side is formed to be flat. As in an illustrated example, when the final surface of lens L3 on the image capturing side is configured by a flat surface, lens unit 35 faces element cover glass 43 with a predetermined distance, adhesive resin 37 is applied thickly to an outer circumferential portion, and thus lens unit 35 is adhered and fixed to element cover glass 43. Here, a distance of separation portion 47 between lens unit 35 and element cover glass 43, for example, is 10 µm to 40 µm according to an error in optical design.

Figure 8:
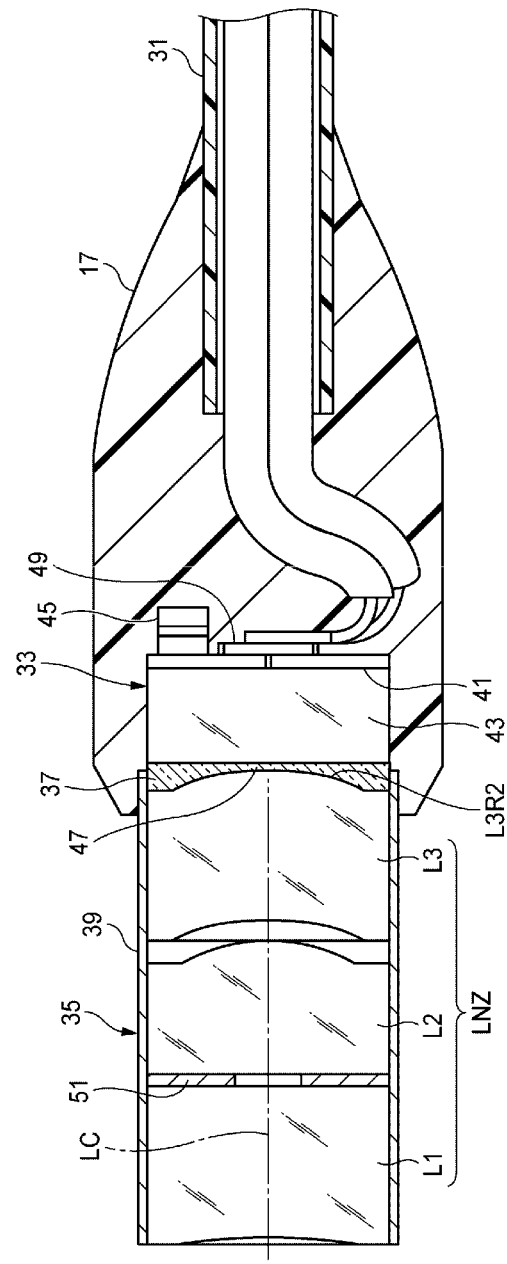
FIG. 8 is a cross-sectional view illustrating a configuration of a leading end portion of an endoscope according to a sixth exemplary embodiment.

FIG. 8 is a cross-sectional view illustrating a configuration of a leading end portion of an endoscope according to a sixth exemplary embodiment. The sixth exemplary embodiment illustrates a fifth modification example of the configuration of the leading end portion of the endoscope.

The endoscope of the sixth exemplary embodiment (the fifth modification example) illustrates another configuration example of lens L3 of lens unit 35. In lens unit 35, first surface L1R1 of lens L1 includes a concave surface, second surface L1R2 includes a flat surface, first surface L2R1 of lens L2 includes a flat surface, second surface L2R2 includes a convex surface, first surface L3R1 of lens L3 which is a final lens includes a concave surface, and second surface L3R2 which is the final lens includes a convex surface in the order from the photographic subject side to the image capturing side.

Separation portion 47 between second surface L3R2 of lens L3 which is the convex surface and element cover glass 43 is filled with adhesive resin 37. According to adhesive resin 37, lens unit 35 is directly adhered and fixed to image capturing element 33. Adhesive resin 37 is configured of a transparent adhesive resin material, and when a refractive index of adhesive resin 37 is nad, and a refractive index of lens L3 is n3, for example, a material satisfying a relationship of |n3−nad|>0.01 is used. That is, the refractive index nad of adhesive resin 37 has as great refractive index difference as possible compared to the refractive index n3 of lens L3 of an end portion on the image capturing side, and specifically, for example, a refractive index nad having a difference greater than 0.01 is preferable. For example, when the refractive index n3 of lens L3 is 1.55, as adhesive resin 37, a material having a refractive index nad of 1.52 is used. Furthermore, when the refractive index difference is able to be ensured, a magnitude relationship between the refractive index n3 of lens L3 and the refractive index nad of adhesive resin 37 may be reversed.

In addition, an interval of separation portion 47 between second surface L3R2 of lens L3 and image capturing surface 41 of image capturing element 33, for example, is 0 to 100 µm in a protruding portion of the center portion of the convex surface of second surface L3R2. That is, the interval is in a dimension range from a state where the center portion of second surface L3R2 is in contact with image capturing surface 41 to a state of being separated by 100 µm. Accordingly, a distance between lens unit 35 and image capturing element 33 in the optical axis direction is adjusted within a range of 0 to 100 µm, and focus position adjustment (focusing) is performed, and thus it is possible to make installation easy.

In addition, at least a part of lens unit 35 on the image capturing side, an outer circumferential portion of image capturing element 33, and the vicinity of the connection portion of transmission cable 31 on the leading end side are sealed by, for example, mold resin 17 having light blocking properties such as a black color as a resin member for sealing. A connection fixation portion between lens unit 35 and image capturing element 33 has a double structure covering an outer circumferential portion of adhesive resin 37 having light transmissivity of a transparent material or the like which transmits light rays of a photographic subject image by disposing mold resin 17 having light blocking properties such as a black color.

In the sixth exemplary embodiment, a refractive index difference between lens L3 and adhesive resin 37 is greater than 0.01, and thus a refraction effect in second surface L3R2 of lens L3 increases. Accordingly, refractive power is able to be obtained by allowing second surface L3R2 of lens L3 which is the final surface of optical lens group LNZ on the image capturing side to effectively function, and the number of optical surfaces which are able to be used in optical lens group LNZ increases. As a result thereof, with respect to an optical performance (resolution, chromatic aberration, distortion, or the like) of optical lens group LNZ, it is possible to reduce the number of lenses for obtaining a necessary optical performance and to promote downsizing and cost reduction. In addition, second surface L3R2 of lens L3 is the convex surface, and adhesive resin 37 is adhered to a curved surface, and thus a contact area of adhesive resin 37 increases and it is possible to improve adhesion strength. In addition, by using the double structure of adhesive resin 37 having light transmissivity and mold resin 17 having light blocking properties, it is possible to improve durability and strength of the leading end portion of the endoscope. In addition, the interval of separation portion 47 in a center portion of lens L3 is 0 to 100 µm, and thus a thickness dimension tolerance of each component of lens unit 35 in the optical axis direction, and an installation dimension tolerance between lens unit 35 and image capturing element 33 are able to be mitigated, assemblability is able to be improved, and the component cost is also able to be reduced.

Figure 9:
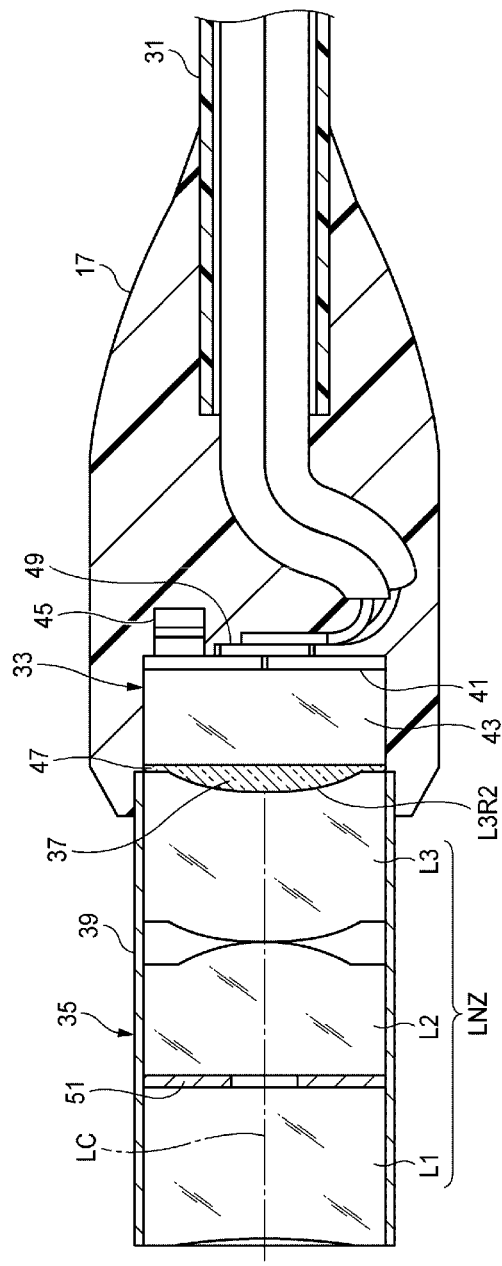
FIG. 9 is a cross-sectional view illustrating a configuration of a leading end portion of an endoscope according to a seventh exemplary embodiment.

FIG. 9 is a cross-sectional view illustrating a configuration of a leading end portion of an endoscope according to a seventh exemplary embodiment. The seventh exemplary embodiment illustrates a sixth modification example of the configuration of the leading end portion of the endoscope.

The endoscope of the seventh exemplary embodiment (the sixth modification example) illustrates still another configuration example of lens L3 of lens unit 35. In lens unit 35, first surface L1R1 of lens L1 includes a concave surface, second surface L1R2 includes a flat surface, first surface L2R1 of lens L2 includes a flat surface, second surface L2R2 includes a convex surface, first surface L3R1 of lens L3 which is the final lens includes a convex surface, and second surface L3R2 which is the final surface includes a concave surface in order from the photographic subject side to the image capturing side. That is, in this configuration example, the concavity and convexity of lens L3 is reversed from that of the sixth exemplary embodiment illustrated in FIG. 8. Here, only a portion having a configuration different from that of the sixth exemplary embodiment will be described.

Separation portion 47 between second surface L3R2 of lens L3 which is the concave surface and element cover glass 43 is filled with adhesive resin 37. The interval of separation portion 47, for example, is 0 to 100 µm in a peripheral portion of the concave surface of second surface L3R2, that is, an edge portion of a lens circumferential edge of second surface L3R2. That is, the interval is in a dimension range from a state where the peripheral portion of second surface L3R2 is in contact with image capturing surface 41 to a state of being separated by 100 μm.

According to the seventh exemplary embodiment, similar to the sixth exemplary embodiment, a refractive index difference between lens L3 and adhesive resin 37 is greater than 0.01, and thus it is possible to reduce the number of lenses for obtaining a necessary optical performance, and it is possible to promote downsizing and cost reduction. In addition, second surface L3R2 of lens L3 is the concave surface, and adhesive resin 37 is adhered to a curved surface, and thus a contact area of adhesive resin 37 increases and it is possible to improve adhesion strength. In addition, the interval of separation portion 47 in the peripheral portion of lens L3 is 0 to 100 μm, and thus a thickness dimension tolerance of each component of lens unit 35 in the optical axis direction, and an installation dimension tolerance between lens unit 35 and image capturing element 33 are able to be mitigated, assemblability is able to be improved, and the component cost is also able to be reduced.

Furthermore, in the sixth exemplary embodiment illustrated in FIG. 8 and in the seventh exemplary embodiment illustrated in FIG. 9, similar to the fourth exemplary embodiment illustrated in FIG. 6B, the air layer may be disposed in a center portion of the lens by adhering only a peripheral portion of lens L3 by the adhesive resin. In this case, it is possible to obtain sufficient refractive power in second surface L3R2 of lens L3 regardless of a refractive index of the adhesive resin.

Here, an example of dimensions of the endoscope of this exemplary embodiment is illustrated. Furthermore, the following numerical values indicate one specific example, and various examples are considered according to use applications, usage environments, or the like.

As an example, lens unit 35 has a length of S=1.4 mm in the front and back direction. In addition, a cross-sectional surface of lens tube 39 is in the shape of a circle having an outer diameter of D=1.00 mm and an inner diameter of d=0.90 mm. In this case, a thickness of lens tube 39 in a diameter direction is (D−d)/2=50 μm. In addition, image capturing element 33 is in the shape of a square of which one side has a length of T=1.00 mm when seen from a front surface, and image capturing surface 41 in the shape of a square when seen from the front surface is disposed in a center portion.

Here, a circle of an outer circumference (an outer diameter=D) of lens tube 39 is approximately in internal contact with a square of image capturing element 33, and is in external contact with a square of image capturing surface 41. Then, positions of the center of image capturing surface 41 (an intersection point of diagonal lines of image capturing surface 41), the center of lens unit 35 (the center of a circle of an inner circumference of lens unit 35), and the center of lens tube 39 (the center of the circle of the outer circumference of lens tube 39) are coincident with each other, and optical axis LC passes therethrough. More accurately, a normal line passing through the center of image capturing surface 41 is optical axis LC, and lens unit 35 is positioned with respect to image capturing element 33 such that optical axis LC passes through the center of lens unit 35.

Next, coating of each of lenses L1, L2, and L3 of lens unit 35 in the first to the seventh exemplary embodiments will be described.

In order to prevent a decrease in light intensity or an occurrence of flare and ghost, a thin film of a single layer or a multi-layer is deposited on the surface of the lens. As a material of the thin film, a metal oxide such as titanium oxide ($TiO_2$), tantalum pentoxide ($Ta_2O_5$), hafnium oxide ($HfO_2$), zirconium oxide ($ZrO_2$), and aluminum oxide ($Al_2O_3$), metal such as silver (Ag), aluminum (Al), and nickel (Ni), silicon oxide ($SiO_2$), silicon carbide (SiC), silicon (Si), magnesium fluoride ($MgF_2$), and the like are used. In addition, generally, in an outermost layer of the single layer or the multi-layer, magnesium fluoride is used in order to obtain an antifouling effect of the outermost surface. However, in the first to the seventh exemplary embodiments, second surface L3R2 which is the final surface of lens L3 which is the final lens is fixed to image capturing element 33 by adhesive resin 37, and when magnesium fluoride is coated to the outermost surface, adhesion strength significantly decreases. For this reason, in the outermost surface of second surface L3R2 of lens L3, a metal oxide, metal, silicon oxide, silicon carbide, silicon, and the like are preferably used in addition to magnesium fluoride.

In addition, by using a silane coupling agent such as trimethylsilane ($C_3H_{10}Si$) which chemically couples an inorganic material and an organic material together in the outermost surface of second surface L3R2 of lens L3, adhesion strength between lens L3 of the inorganic material and adhesive resin 37 of the organic material may increase.

Next, a manufacturing method (a manufacturing process of leading end portion 15) of endoscope 11 of this exemplary embodiment having the configuration described above will be described.

Figure 10A:
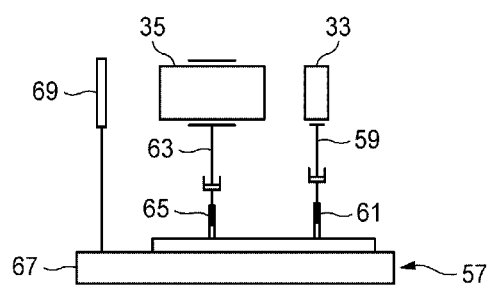
FIG. 10A is a configuration diagram of a position adjustment jig in a first example of a manufacturing method of an endoscope.
Figure 10B:
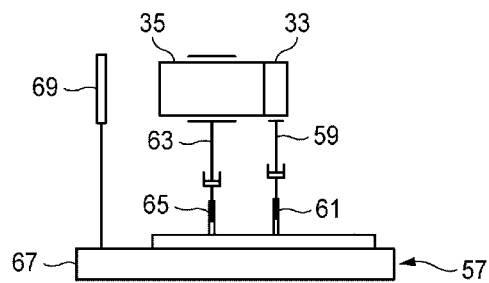
FIG. 10B is a side view at the time of fixing a lens unit to an image capturing element in the first example.
Figure 10C:
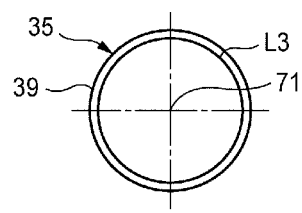
FIG. 10C is an explanatory diagram of a projected image at the time of performing positioning in an XY direction in the first example.
Figure 10D:
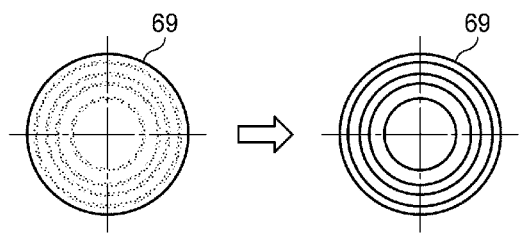
FIG. 10D is an explanatory diagram of a projected image at the time of performing positioning in a Z direction in the first example.

FIGS. 10A and 10B are diagrams illustrating a first example of a manufacturing method of an endoscope, FIG. 10A is a configuration diagram of a position adjustment jig, FIG. 10B is a side view at the time of fixing the lens unit to the image capturing element, FIG. 10C is a diagram illustrating a projected image at the time of performing positioning in an XY direction, and FIG. 10D is an explanatory diagram of a projected image at the time of performing positioning in a Z direction. Furthermore, here, the XY direction indicates right-left and up-down directions illustrated in FIG. 1, and the Z direction indicates the front and back direction illustrated in FIG. 1.

In the first example of the manufacturing method of an endoscope, by using position adjustment jig 57, a back end of lens unit 35 is fixed to be blocked by image capturing element 33. Position adjustment jig 57 includes sensor support portion 59, first XYZ stage 61, lens unit support portion 63, second XYZ stage 65, flat surface base 67, and test chart 69.

Sensor support portion 59 supports a lower surface of image capturing element 33. First XYZ stage 61 maintains sensor support portion 59 and is able to perform position adjustment in the front-back and right-left directions and the up and down direction (it is preferable to use a microstage). Lens unit support portion 63 horizontally supports lens unit 35 from both side surfaces. Second XYZ stage 65 maintains lens unit support portion 63 and is able to perform position adjustment in the front-back and right-left directions and the up and down direction. Test chart 69 is a photographic subject of lens unit 35, and has a pattern to which vignetting and a focus of the photographic subject image due to image capturing is able to refer. Flat surface base 67 commonly supports test chart 69, and sensor support portion 59 and lens unit support portion 63.

Leading end portion 15 is assembled by using position adjustment jig 57 described above, and basically, leading end portion 15 is manually assembled by an operator using a microscope.

First, adhesive resin 37 is applied to at least one of lens unit 35 and image capturing element 33 in advance. Then, lens unit 35 is supported, and the optical axis of lens unit 35 and the center of image capturing surface 41 of image capturing element 33 are positioned with reference to an image captured by image capturing element 33 while moving image capturing element 33 supported on first XYZ stage 61. Specifically, for example, as illustrated in FIG. 10C, the center of lens tube 39 and lens L3, and projected image center 71 are positioned. The projected image of image capturing element 33 is obtained by placing a probe (not illustrated) on a terminal of image capturing element 33 to extract an image signal, and by displaying the image on a display device (not illustrated).

Subsequently, a direction along the optical axis of lens unit 35 and image capturing element 33 is positioned. In this positioning step, as illustrated in FIG. 10D, by adjusting a position of lens unit 35 in the front and back direction, incident light from test chart 69 is focused on image capturing surface 41 of image capturing element 33. That is, as illustrated in FIG. 10B, focusing is performed by adjusting the position of lens unit 35 in a direction of optical axis LC.

At the time of performing the position adjustment of lens unit 35, transmission cable 31 and circuit substrate 49 may be or may not be connected to each other. When transmission cable 31 and circuit substrate 49 are not connected to each other, as described above, the probe is placed on the terminal of image capturing element 33 to extract the image signal, and thus a photographic subject image for a test is displayed on the display device.

On the other hand, when transmission cable 31 is connected to image capturing element 33, an output of image capturing element 33 is processed by video processor 19 described above, and thus the image is able to be displayed on the display device. By using a predetermined test chart 69 (for example, a resolution chart) as the photographic subject, the position adjustment of lens unit 35 is easily performed, and it is possible to reduce the time required for the positioning step.

In a step where the position adjustment of lens unit 35 and image capturing element 33 is completed, it is preferable that adhesive resin 37 is slightly exposed from a space between lens unit 35 and image capturing element 33. When an amount of adhesive resin 37 is not sufficient, adhesive resin 37 is injected into the space between lens unit 35 and image capturing element 33. The space between lens unit 35 and image capturing element 33 is filled with the injected adhesive resin 37 by a capillary action.

After positioning image capturing element 33 on the back end of lens unit 35, adhesive resin 37 is cured by ultraviolet irradiation, and lens unit 35 is temporarily fixed to image capturing element 33 by adhesive resin 37. The ultraviolet irradiation is performed with respect to the exposed adhesive resin 37 in a state where a relative front and back position of lens unit 35 and image capturing element 33 is maintained. Adhesive resin 37 is cured by the ultraviolet irradiation, and thus image capturing element 33 is temporarily fixed in the vicinity of the back end of lens unit 35. Adhesive resin 37 is cured by the ultraviolet irradiation for a short period of time such as a few seconds, and thus it is possible to reduce the time required for a process. Lens unit 35 and image capturing element 33 which are temporarily fixed are detached from position adjustment jig 57.

After that, adhesive resin 37 is further cured by heat treatment, and lens unit 35 and image capturing element 33 are permanently fixed by adhesive resin 37. Adhesive resin 37 is cured by the heat treatment, and thus lens unit 35 and image capturing element 33 are strongly fixed.

Subsequently, leading end portion 15 is subjected to mold processing by which the back portion of lens unit 35 and image capturing element 33 are covered with mold resin 17. In a mold processing step, mold resin 17 is applied and secured to lens unit 35 in order to cover at least image capturing element 33 positioned on a back side from the back end of lens unit 35, and circuit substrate 49 and the leading end of transmission cable 31 (an electric connection portion with respect to image capturing element 33), and thus a sealing portion is configured.

At this time, mold resin 17 is also applied to the back end of lens unit 35 across the front surface of image capturing element 33, and thus separation portion 47 is reliably blocked. Mold resin 17 used herein has high viscosity to the extent of covering at least image capturing element 33, circuit substrate 49, the leading end of transmission cable 31, and a gap, and is applied mainly for sealing by which moisture is prevented from invading the inner portion of leading end portion 15 from the back side from image capturing element 33 and separation portion 47.

In addition, in order to easily produce an illustrated shape by using mold resin 17, the sealing portion may be formed by using a resin mold. In this case, the resin mold (not illustrated) is arranged to cover from the back end of lens unit 35 to the leading end of transmission cable 31 in advance, mold resin 17 is casted and cured, and the resin mold is removed.

As mold resin 17, various known adhesive agents are able to be used, and for example, an adhesive agent of a thermosetting resin such as an epoxy resin and an acrylic resin may be used. Further, it is preferable to adopt a black resin containing carbon particles in these resins. Accordingly, it is possible to prevent stray light from the outside from being incident on image capturing surface 41 of image capturing element 33.

After that, leading end portion 15 is placed under an environment of 60° C. to 80° C. for approximately 30 minutes, and thus mold resin 17 covering image capturing element 33, circuit substrate 49, the leading end of transmission cable 31, and separation portion 47 is completely cured. When the mold processing step is finished, assembling of leading end portion 15 of endoscope 11 is completed.

Figure 11A:
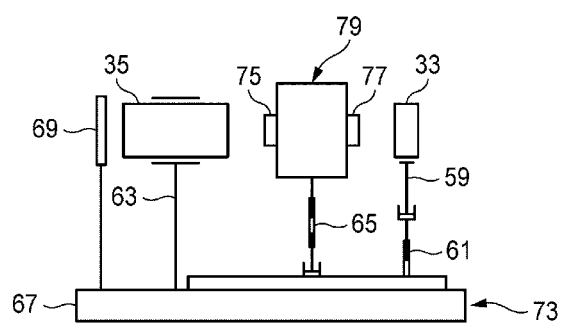
FIG. 11A is a configuration diagram of a camera attached position adjustment jig in a second example of the manufacturing method of an endoscope.
Figure 11B:
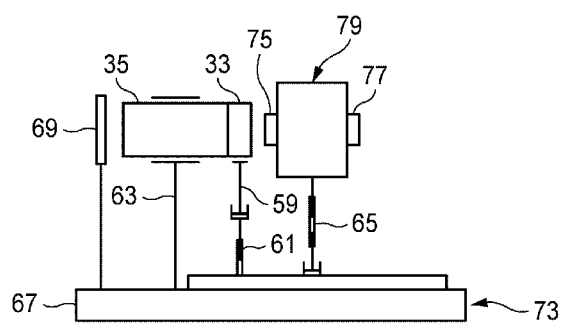
FIG. 11B is a side view at the time of fixing a lens unit to an image capturing element in the second example.
Figure 11C:
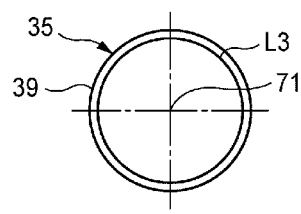
FIG. 11C is an explanatory diagram of a projected image at the time of performing positioning using a second camera in the second example.
Figure 11D:
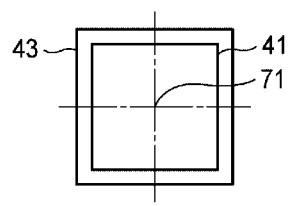
FIG. 11D is an explanatory diagram of a projected image at the time of performing positioning using a first camera in the second example.
Figure 11E:
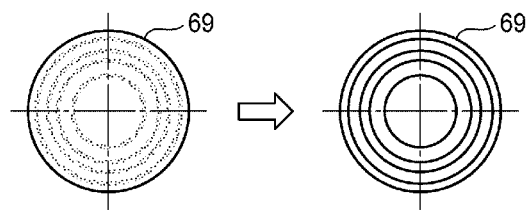
FIG. 11E is an explanatory diagram of a projected image at the time of performing positioning in a Z direction in the second example.

FIGS. 11A and 11B are diagrams illustrating a second example of the manufacturing method of an endoscope, FIG. 11A is a configuration diagram of a camera attached position adjustment jig, FIG. 11B is a side view at the time of fixing the lens unit to the image capturing element, FIG. 11C is an explanatory diagram of a projected image at the time of performing positioning using a second camera, FIG. 11D is an explanatory diagram of a projected image at the time of performing positioning using a first camera, and FIG. 11E is an explanatory diagram of a projected image at the time of performing positioning in the Z direction. Furthermore, the same reference numeral is applied to the same member as the member illustrated in FIGS. 10A to 10D, and the repeated description will be omitted. Similar to the first example, the XY direction indicates the right-left and up-down directions illustrated in FIG. 1, and the Z direction indicates the front and back direction illustrated in FIG. 1.

In the second example of the manufacturing method of an endoscope, by using camera attached position adjustment jig 73, the back end of lens unit 35 is fixed to be blocked by image capturing element 33. Camera attached position adjustment jig 73 includes a first moving image camera attached microscope (hereinafter, referred to as "first camera 77") observing image capturing element 33 from a front side, and a second moving image camera attached microscope (hereinafter, referred to as "second camera 75") observing lens unit 35 from a back side.

First camera 77 and second camera 75 are integrated with each other and are able to simultaneously capture right and left images (or up and down images, and front and back images). Hereinafter, such a camera having an integrated configuration is referred to as "right and left camera 79". An image capturing direction is different approximately 180 degrees in a state where optical axes of the respective first camera 77 and second camera 75 are aligned with each other with extremely high accuracy. Right and left camera 79 is attached to second XYZ stage 65, and is arranged between sensor support portion 59 of the camera attached position adjustment jig 73 and lens unit support portion 63. Sensor support portion 59 is supported on first XYZ stage 61. First XYZ stage 61, second XYZ stage 65, and lens unit support portion 63 are disposed in flat surface base 67. Test chart 69 is attached to flat surface base 67.

In camera attached position adjustment jig 73, parallelism between sensor support portion 59 supported on first XYZ stage 61 and lens unit support portion 63 is adjusted in advance, and is aligned with high accuracy. Furthermore, at the time of mounting image capturing element 33, a bottom surface of image capturing element 33 is temporarily fixed to sensor support portion 59. As a method of temporarily fixing the bottom surface, for example, image capturing element 33 may be vacuum sucked by forming a plurality of micropores in sensor support portion 59, and by connecting the micropores to a vacuum pump.

Leading end portion 15 is assembled by using camera attached position adjustment jig 73 described above, and basically, leading end portion 15 is manually assembled by the operator using a microscope. First, adhesive resin 37 is applied to at least one of lens unit 35 and image capturing element 33 in advance.

Then, as illustrated in FIG. 11A, right and left camera 79 including first camera 77 and second camera 75 of which the optical axes are coincident with each other is arranged between image capturing element 33 and lens unit 35. Subsequently, as illustrated in FIG. 11D, the center of image capturing surface 41 of image capturing element 33 is moved to projected image center 71 with reference to a projected image captured by first camera 77. Then, as illustrated in FIG. 11C, the center of lens unit 35 is moved to projected image center 71 with reference to a projected image captured by second camera 75. After that, as illustrated in FIG. 11B, after right and left camera 79 is retracted, as illustrated in FIG. 11E, the distance between lens unit 35 and image capturing element 33 in the direction along the optical axis is adjusted with reference to a projected image captured by image capturing element 33.

In the positioning step, a position of second XYZ stage 65 is adjusted with reference to a projected image obtained by capturing an image of the back end of lens unit 35 by second camera 75, and thus right and left camera 79 (accurately, the optical axis of right and left camera 79) is aligned with the center of lens unit 35 (a center position in the diameter direction). A right and left position of first XYZ stage 61 is adjusted with reference to a projected image captured by first camera 77, and thus the center of image capturing surface 41 of image capturing element 33 supported on sensor support portion 59 is moved to the center of XY coordinates on a screen, that is, the center position of lens unit 35. Accordingly, even when the center of image capturing surface 41 of image capturing element 33, that is optical axis LC varies according to solid, lens unit 35 and image capturing element 33 are able to be positioned on the basis of optical axis LC.

Then, right and left camera 79 is retracted from a space between sensor support portion 59 and lens unit support portion 63, the front and back position of first XYZ stage 61 is adjusted, and image capturing element 33 supported on sensor support portion 59 is in contact with the back end of lens unit 35.

After, image capturing element 33 is positioned on the back end of lens unit 35 by the operation described above, similar to the first example, an applied portion of adhesive resin 37 which is exposed is irradiated with ultraviolet rays, and adhesive resin 37 is cured, and thus lens unit 35 is temporarily fixed to image capturing element 33 by adhesive resin 37. Thus, image capturing element 33 is positioned and then mounted on the back end of lens unit 35.

After that, similar to the first example, by performing heat treatment, lens unit 35 is permanently fixed to image capturing element 33 by adhesive resin 37. Subsequently, similar to the first example, the mold processing is performed, and the assembling of leading end portion 15 of endoscope 11 is completed.

Next, an action of endoscope 11 of this exemplary embodiment having the configuration described above will be described.

In endoscope 11 according to this exemplary embodiment, lens unit 35 is fixed to image capturing element 33 by adhesive resin 37 in a state where a predetermined distance is maintained. In fixed lens unit 35 and image capturing element 33, the optical axis of lens unit 35 and the center of image capturing surface 41 are positioned. In addition, the distance between lens unit 35 and image capturing element 33 is positioned to be a distance in which incident light through lens unit 35 from the photographic subject is focused on image capturing surface 41 of image capturing element 33. Lens unit 35 and image capturing element 33 are positioned and then fixed.

Separation portion 47 is formed between fixed lens unit 35 and image capturing element 33. Lens unit 35 and image capturing element 33 are relatively positioned, and are fixed to each other by adhesive resin 37, and thus the shape of separation portion 47 is determined. That is, separation portion 47 is an adjustment gap for positioning lens unit 35 and image capturing element 33. The adjustment gap may not be included. In the specific example of the dimension described above, an adjustment is performed at least from approximately 30 μm to approximately 100 μm. At this time, a tolerance is ±20 μm. Accordingly, the minimum adjustment gap of this case is 10 μm.

In endoscope 11, after separation portion 47 is the adjustment gap and the positioning of lens unit 35 and image capturing element 33 is completed, separation portion 47 is used for a fixed space of adhesive resin 37. Accordingly, lens unit 35 is able to be directly fixed to image capturing element 33. Accordingly, an interposing member such as a frame or a holder for fixing lens unit 35 to image capturing element 33 which has been required in the related art is not required. In addition, the frame, the holder, or the like is able to be omitted, and thus the number of components is reduced, and a fixed structure is simplified. Accordingly, the diameter of leading end portion 15 of endoscope 11 is able to be decreased, and even when a reduction in the diameter is promoted, leading end portion 15 is able to be configured in the minimum dimensions. In addition, the component cost is also able to be reduced. Further, the number of interposing components at the time of fixing lens unit 35 to image capturing element 33 decreases, and thus it is possible to reduce the number of man-hours required for the operations relevant to the positioning and the fixing, and it is possible to easily perform the positioning with high accuracy. In addition, it is possible to reduce the manufacturing cost, and it is possible to improve productivity.

In addition, in endoscope 11, the entire image capturing element 33 is covered with mold resin 17. More specifically, mold resin 17 also covers an external portion of transmission cable 31 connected to image capturing element 33. Mold resin 17 also covers at least a part of lens unit 35 (an adjacent portion with respect to image capturing element 33). The expression "at least" indicates that mold resin 17 may cover the entire outer circumference of lens tube 39. Mold resin 17 covers image capturing element 33 and lens unit 35, and thus also continuously covers separation portion 47 therebetween. Accordingly, mold resin 17 is continuously formed across image capturing element 33 and lens unit 35, and thus contributes to an increase in fixation strength between image capturing element 33 and lens unit 35. In addition, mold resin 17 also increases airtightness, liquidtightness, and light blocking properties of separation portion 47. Further, mold resin 17 also increases light blocking properties when an optical fiber for light guidance is embedded.

In addition, in endoscope 11, element cover glass 43 is fixed to a light emitting surface of the lens on the image capturing element side by adhesive resin 37. Accordingly, lens unit 35 is fixed to image capturing element 33 by adhesive resin 37 with high strength.

Adhesive resin 37 has light transmissivity, and it is preferable that a refractive index of adhesive resin 37 is close to that of air. When a UV thermosetting resin is used as adhesive resin 37, an outer portion of the filled adhesive agent is able to be cured by ultraviolet irradiation, and an inner portion of the filled adhesive agent which is not able to be irradiated with ultraviolet rays is able to be cured by heat treatment.

In addition, in endoscope 11, when the light emitting surface of the lens facing element cover glass 43 is a concave surface, annular cross-sectional surface (an edge portion) 55 around the lens is adhered to element cover glass 43. At this time, the outer circumference of the lens, and the outer circumference of lens tube 39 may be simultaneously fixed by adhesive resin 37. Air layer 53 is disposed between the lens and image capturing element 33, and thus it is possible to improve an optical performance of the lens. For example, it is possible to increase a refractive index of emitted light from the lens to air layer 53. Accordingly, resolution increases, and thus an optical design such as increasing a field angle is facilitated. As a result thereof, image quality is improved.

In a first manufacturing method of endoscope 11 according to this exemplary embodiment, lens unit 35 and image capturing element 33 are positioned according to the output of image capturing element 33 by using position adjustment jig 57, and an additional camera for positioning or the like is not used. Thus, it is possible to directly use the projected image obtained by image capturing element 33, and thus it is possible to easily perform position adjustment. Then, it is possible to directly fix lens unit 35 to image capturing element 33 which are positioned. Accordingly, it is possible to decrease the number of man-hours of a fixation operation, and it is possible to reduce operation time. In addition, it is possible to perform positioning of high accuracy without interposing a plurality of members.

In a second manufacturing method of endoscope 11 according to this exemplary embodiment, the image of each of lens unit 35 and image capturing element 33 is captured, and lens unit 35 and image capturing element 33 are positioned by using the camera attached position adjustment jig 73. Accordingly, even when the center of image capturing surface 41 of image capturing element 33, that is the optical axis varies according to the solid, lens unit 35 and image capturing element 33 are able to be positioned on the basis of the optical axis of right and left camera 79.

As described above, according to endoscope 11 and the manufacturing method of endoscope 11 according to this exemplary embodiment, it is possible to promote downsizing, cost reduction, and productivity improvement.

According to the examples described above, after the separation portion is the adjustment gap and the positioning of the lens unit and the image capturing element is completed, the separation portion is used for the fixed space of the adhesive resin. Accordingly, the lens unit is able to be directly fixed to the image capturing element. Accordingly, the interposing member such as the frame or the holder for fixing the lens unit to the image capturing element which has been required in the related art is not required. In addition, the number of components is reduced, and the fixed structure is simplified. In addition, the number of interposing components decreases, and thus it is possible to reduce the number of man-hours required for the fixation operation, and it is possible to easily perform the positioning with high accuracy. As a result thereof, it is possible to reduce the diameter of the leading end portion of the endoscope. In addition, it is possible to reduce the manufacturing cost, and it is possible to improve productivity.

According to the examples described above, the entire image capturing element is covered with the mold resin. More specifically, the mold resin also covers the external portion of the transmission cable connected to the image capturing element. The mold resin also covers at least a part of the lens unit (the adjacent portion with respect to the image capturing element). The expression "at least" indicates that the mold resin may cover the entire outer circumference of the lens tube. The mold resin covers the image capturing element and the lens unit, and thus also continuously covers the separation portion therebetween. Accordingly, the mold resin is continuously formed across the image capturing element and the lens unit, and thus contributes to an increase in fixation strength between the image capturing element and the lens unit. In addition, the mold resin also increases airtightness, liquidtightness, and light blocking properties of the separation portion. Further, the mold resin also increases light blocking properties when the optical fiber for light guidance is embedded.

According to the examples described above, the element cover glass is fixed to the light emitting surface of the lens on the image capturing element side by the adhesive resin. Accordingly, the lens unit is fixed to the image capturing element by the adhesive resin with high strength. As the adhesive resin, an adhesive resin having light transmissivity and a refractive index close to that of air is used. In this case, as the adhesive resin, a UV thermosetting resin is preferably used. According to the UV thermosetting resin, the inner portion of the filled adhesive agent which is not able to be irradiated with ultraviolet rays is able to be cured by heat treatment.

According to the examples described above, when the light emitting surface of the lens facing the element cover glass is a concave surface, the annular cross-sectional surface around the lens is adhered to the element cover glass. At this time, the outer circumference of the lens, and the outer circumference of the lens tube may be simultaneously fixed by the adhesive resin. The air layer is disposed between the lens and the image capturing element, and thus it is possible to improve an optical performance of the lens. For example, it is possible to increase a refractive index of the emitted light from the lens to the air layer. Accordingly, resolution increases, and thus the optical design such as increasing a field angle is facilitated. As a result thereof, image quality is improved.

According to the examples described above, the concave surface or the convex surface of the final surface of the lens unit has refractive power, and thus it is possible to reduce the number of lenses for obtaining a necessary optical performance, and it is possible to promote downsizing and cost reduction. In addition, the adhesive resin is adhered to the curved surface, and thus a contact area of the adhesive resin increases and adhesion strength is improved.

According to the examples described above, refractive power is able to be obtained by allowing the concave surface or the convex surface of the final surface of the lens unit to effectively function, and the number of optical surfaces which are able to be used in the optical lens group increases, and thus it is possible to reduce the number of lenses for obtaining a necessary optical performance and to promote downsizing and cost reduction.

According to the examples described above, a thickness dimension tolerance of each component of the lens unit in the optical axis direction, and an installation dimension tolerance between the lens unit and the image capturing element is able to be mitigated, and thus assemblability is able to be improved, and the component cost is also able to be reduced.

According to the examples described above, when the lens unit is fixed to the image capturing element by the adhesive resin, it is possible to prevent adhesion strength from being decreased.

According to the examples described above, the additional camera for positioning or the like is not used by using the output of the image capturing element. It is possible to easily perform the position adjustment by directly using the projected image obtained by the image capturing element. Then, it is possible to directly fix the lens unit and the image capturing element which are used for obtaining the projected image. Accordingly, it is possible to decrease the number of man-hours of a fixation operation, and it is possible to reduce operation time. It is possible to perform positioning of high accuracy without interposing a plurality of members.

According to the examples described above, even when the center of the image capturing surface of the image capturing element, that is, the optical axis varies according to the solid, the lens unit and the image capturing element are able to be positioned on the basis of the optical axis of the right and left camera.

As described above, various exemplary embodiments are described with reference to the drawings, but the present invention is not limited to such an example. It is obvious that a person skilled in the art is able to conceive various change examples or correction examples in a category described in the Claims, and it is understood that these change examples or correction examples naturally belong to the technical range of the present invention. In addition, the respective constituents in the exemplary embodiment described above may be arbitrarily combined within a range not deviating from the gist of the invention.

What is claimed is:

1. An endoscope, comprising:
   a lens unit containing a lens in a lens tube, the lens including an optical axis;
   an image capturing element including an image capturing surface which is covered with an element cover glass, the optical axis of the lens being coincident with a center of the image capturing surface;
   an adhesive resin fixing an image capturing element side of the lens in the lens unit to the element cover glass and fixing an image capturing element side of the lens tube to the element cover glass, the adhesive resin being a light transmitting material;
   a separation portion between the lens unit and the element cover glass; and
   a mold resin covering the image capturing element and at least a part of the lens unit, the mold resin being a light blocking material.

2. The endoscope of claim 1,
   wherein the separation portion is filled with an adhesive resin.

3. The endoscope of claim 1,
   wherein an air layer transmitting light from the lens is disposed in the separation portion.

4. The endoscope of claim 1,
   wherein the image capturing element side of the lens includes a concave surface or a convex surface.

5. The endoscope of claim 4,
   wherein the separation portion is filled with the adhesive resin, and
   a refractive index of the lens and a refractive index of the adhesive resin have a refractive index difference greater than or equal to a predetermined value.

6. The endoscope of claim 4,
   wherein the lens unit is adhered and fixed to the image capturing element with a distance of a predetermined range in an optical axis direction in the separation portion.

7. The endoscope of claim 1,
   wherein an outermost surface of the lens on the image capturing element side of the lens is magnesium fluoride.

8. The endoscope of claim 1,
   wherein an outermost surface of the lens on the image capturing element side of the lens is any one of a metal oxide, metal, silicon oxide, silicon carbide, and silicon.

9. The endoscope of claim 1,
   wherein an outermost surface of the lens on the image capturing element side of the lens is a silane coupling agent.

10. A manufacturing method of an endoscope, comprising:
    applying a UV thermosetting resin to at least one of a lens unit containing a lens in a lens tube, the lens including an optical axis, and an image capturing element which includes an image capturing surface covered with an element cover glass;
    supporting the lens unit;
    positioning the optical axis of the lens unit and a center of the image capturing surface of the image capturing element by referring to an image captured by the image capturing element while moving the image capturing element supported on an XYZ stage;
    adjusting a position of the lens unit relative to the image capturing element along the optical axis of the lens unit;

temporarily fixing the lens unit to the image capturing element with the UV thermosetting resin by ultraviolet irradiation;

permanently fixing an image capturing element side of the lens in the lens unit to the element cover glass of the image capturing element and permanently fixing an image capturing side of the lens tube to the element cover glass of the image capturing element with the UV thermosetting resin by heat treatment, the heat treated UV thermosetting resin being a light transmitting material; and covering the image capturing element and at least a part of the lens unit with a mold resin, the mold resin being a light blocking material.

11. A manufacturing method of an endoscope, comprising:

applying a UV thermosetting resin to at least one of a lens unit containing a lens in a lens tube, the lens including an optical axis, and an image capturing element which includes an image capturing surface covered with an element cover glass;

arranging a right and left camera including a first camera and a second camera of which optical axes are coincident with each other between the image capturing element and the lens unit;

moving the center of an image capturing surface of the image capturing element onto the center of a screen by referring to a projected image captured by the first camera;

moving the center of the lens unit onto the center of the screen by referring to a projected image captured by the second camera;

adjusting a distance in a direction along the optical axis of the lens unit and the image capturing element by referring to a projected image captured by the image capturing element after retracting the right and left camera;

temporarily fixing the lens unit to the image capturing element with the UV thermosetting resin by ultraviolet irradiation;

permanently fixing an image capturing element side of the lens in the lens unit to the element cover glass of the image capturing element and permanently fixing an image capturing side of the lens tube to the element cover glass of the image capturing element with the UV thermosetting resin by heat treatment, the heat treated UV thermosetting resin being a light transmitting material; and covering the image capturing element and at least a part of the lens unit with a mold resin, the mold resin being a light blocking material.

\* \* \* \* \*